United States Patent [19]

Marshall

[11] Patent Number: 4,865,382

[45] Date of Patent: Sep. 12, 1989

[54] SURGEON'S OPERATING STOOL

[76] Inventor: William H. Marshall, Hillcrest Medical Plaza, 420 NE. Glen Oak, Peoria, Ill. 61603

[21] Appl. No.: 252,397

[22] Filed: Oct. 3, 1988

[51] Int. Cl.$^4$ .......................... A47D 13/04; B62J 1/00; A47C 1/02

[52] U.S. Cl. .................................. 297/195; 248/157; 248/188.2; 297/5; 297/339

[58] Field of Search .............. 297/195, 241, 339, 330, 297/5; 248/415, 157, 188.2; 182/15

[56] References Cited

U.S. PATENT DOCUMENTS

| | | | |
|---|---|---|---|
| 3,911,509 | 10/1975 | Fleckenstein | 182/15 X |
| 3,963,096 | 6/1976 | Jones | 182/15 |
| 4,155,423 | 5/1979 | Miller | 182/15 X |
| 4,183,579 | 1/1980 | Gonzalez | 297/195 |
| 4,366,981 | 1/1983 | Ziegler et al. | 297/195 |
| 4,552,404 | 11/1985 | Congleton | 297/330 |

Primary Examiner—James T. McCall
Attorney, Agent, or Firm—Sixbey, Friedman, Leedom & Ferguson

[57] ABSTRACT

A surgeon's operating stool 10 is provided which is readily movable when not occupied by a person but resists undesirable movement once a person has occupied the stool 10. The stool is provided with a series of rollers 20 which normally support the stool 10 and allow for movement in any desired direction. However, the rollers 20 include a spring loaded collapsible mechanism which, when occupied by a person, forces the rollers 20 to retract into the base 12 of the stool 10 and causes a nonskin surface 38 to engage the floor. The base 12 of the stool 10 is configured to receive the feet of a person using the stool, such that a person using the stool in either a standing or sitting position forces the retracting mechanism to remain retracted and thereby prevent undesirable movement during use. The stool 10 also includes a hydraulic height adjusting mechanism which is readily adjustable via foot operation. It is of particular importance in a sterile environment that a surgeon be capable of readily adjusting the stool 10 height without use of his sterilized hands. Further, a rotary coupling 28 interconnects a seat 26 and the support rod 22 of the stool 10 such that the seat 26 is free to rotate in a plane substantially parallel to the floor.

20 Claims, 2 Drawing Sheets

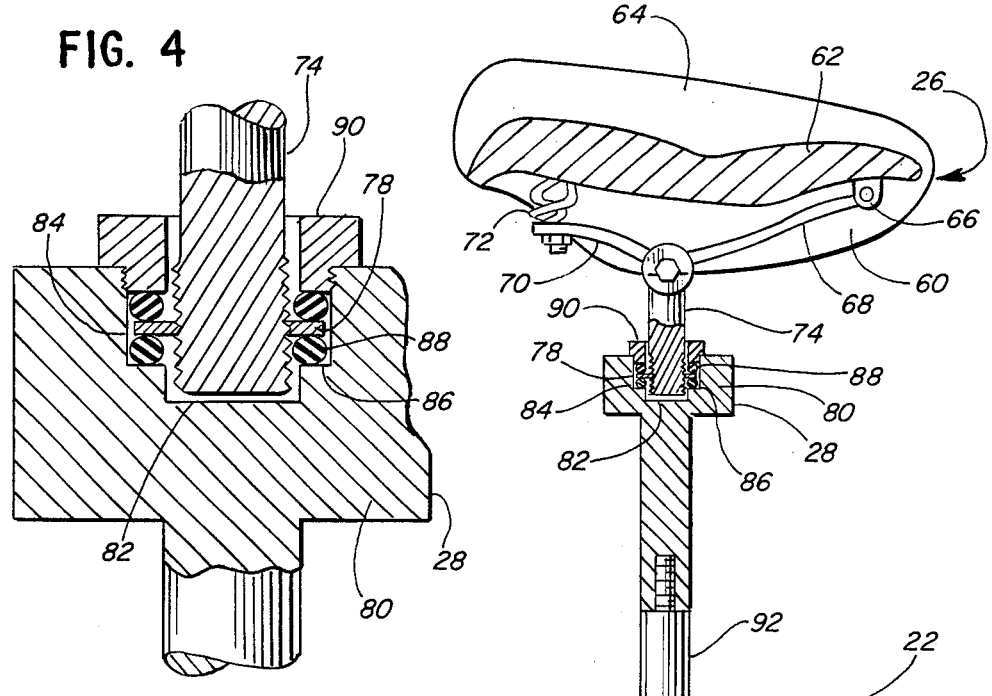
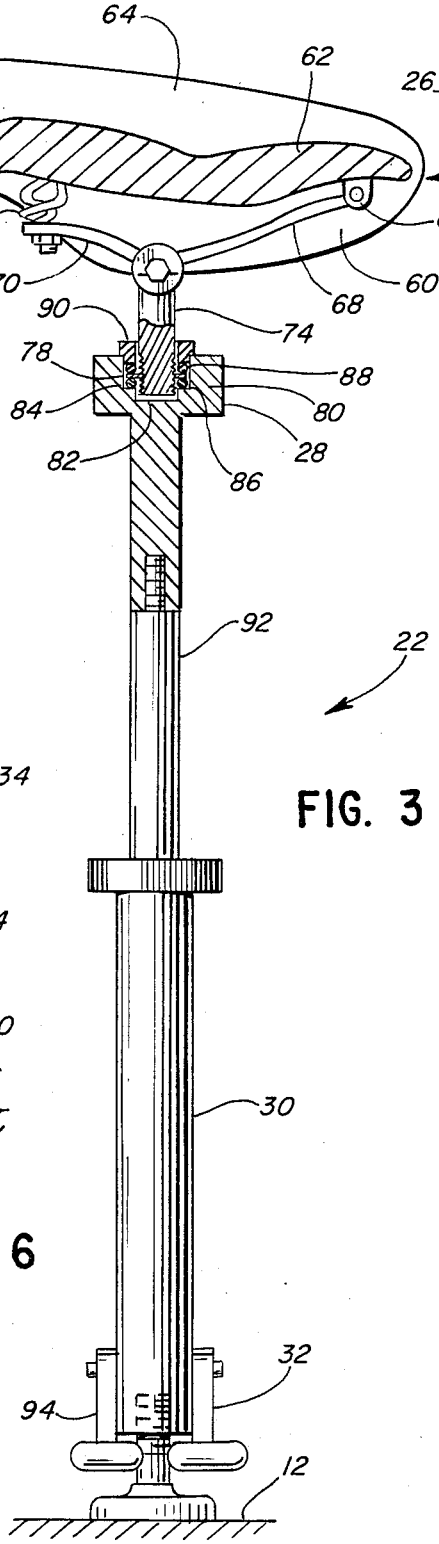
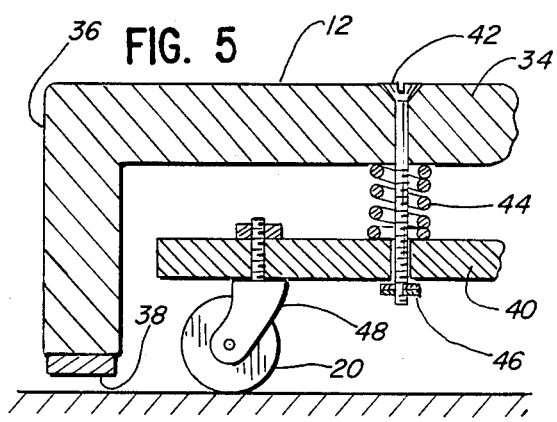
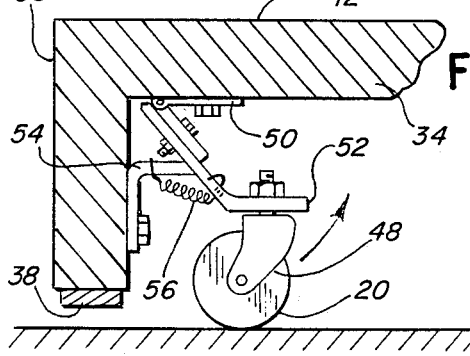

SURGEON'S OPERATING STOOL

BACKGROUND OF THE INVENTION

1. Field of the Invention

This invention relates generally to a stool for use by a surgeon in an operating room, and more particularly, to an operating stool which is readily adjustable in height and position and adapted for carrying the weight of the surgeon in a standing or sitting position.

2. Description of the Related Art

Medical technology in the twentieth century has seen advances unparalleled in the entire previous history of mankind. These advances have generally been of a technical nature providing the doctor with better tools and better drugs to treat his patients. Certainly, the doctors of today are better trained than their counterparts in prior history. However, the same basic human limitations which limited the performance of doctors in the last century are still involved in all medical procedures today.

For example, medical technology has advanced to the point where individual blood vessels no larger than a human hair may be sewn together. However, it is still the doctor who places the stitches in the blood vessel. Although technology has aided the surgeon with powerful magnifying lenses, it is still the human hand which performs the work. Similarly, x-rays, cat scans, or the myriad of medical tests performed daily are of little use without the trained doctor to interpret the results.

Accordingly, along with these great advances in medical technology, there must be corresponding advances in those devices which aid the doctor to carry out his required physical tasks.

Physical limitations of modern doctors is most evident in the operating room. Here more than anywhere else the health of a patient is directly affected by the physical skills of his or her doctor. Consider, for example, the complex microsurgery associated with reattaching a limb. This type of surgery can often last as long as 12 hours. The problems associated with surgeon fatigue during such a long operation are apparent. The physical demand normally placed on the surgeon are exacerbated by the extended time and exacting nature of such surgery.

The nature of an operation dictates that a surgeon will ordinarily assume a variety of positions in order to gain access to the patient. Commonly, the surgeon must stand, leaning over the patient, but occasionally changing positions to optimize view, leverage, and comfort. Accordingly, prior surgeon's stools have been suggested which attempt to provide support and stability and yet maintain portability. For example, U.S. Pat. No. 2,678,684 issued May 18, 1954 to Thomson discloses a rollable operating stool which includes a crude mechanical brake. The surgeon engages the brake by tipping the entire stool until the brake engages the floor. Such a precarious balancing act is not likely to improve the comfort or endurance of a surgeon performing extended and delicate procedures.

Accordingly, it is desired that an operating stool be provided which is comfortable, easy to use, and yet maintains the sterile nature of the operating room environment.

SUMMARY OF THE INVENTION

The primary object of the invention is to provide an operating stool which is adjustable to an infinite variety of positions without requiring the use of the surgeon's sterilized hands.

Another object of the present invention is to provide an operating stool which is readily movable when desired but is relatively fixed against movement during use by the surgeon.

Yet, another object of the present invention is to provide an operating stool which has a base that is sufficiently low in height to extend under the operating table and allow the surgeon to approach within close proximity to the operating table.

To attain these and other objectives, a surgeon's operating stool is provided which supports a user in both standing and sitting positions. A flat substantially planar base has upper and lower surfaces. The upper surface is generally configured to receive the feet of a person using the stool in both a standing and sitting position. A support rod has first and second and portions. The first end portion extends from the upper surface of the base generally perpendicular to the base. The second end portion is connected to a seat. A plurality of multidirectional rollers are positioned below the lower surface of the base. The rollers and the base are movable between first and second preselected positions in response to the presence of a person on the stool. The first position is with the wheels in contact with a support surface and the base being positioned at a preselected distance above the support surface. The second position is with both the wheels and the lower surface of the base being in contact with the support surface.

BRIEF DESCRIPTION OF THE DRAWINGS

Other objects and advantages of the invention will become apparent upon reading the following detailed description and upon reference to the drawings, in which:

FIG. 3 is a side view of the operating stool with portions of the support rod and seat in cross-section;

FIG. 4 is an enlarged view of the support rod with parts broken away in order to illustrate the bearing mechanism;

FIG. 5 illustrates one embodiment of the collapsible roller mechanism; and

FIG. 6 illustrates an alternative embodiment of the collapsible mechanism.

Figure 1:
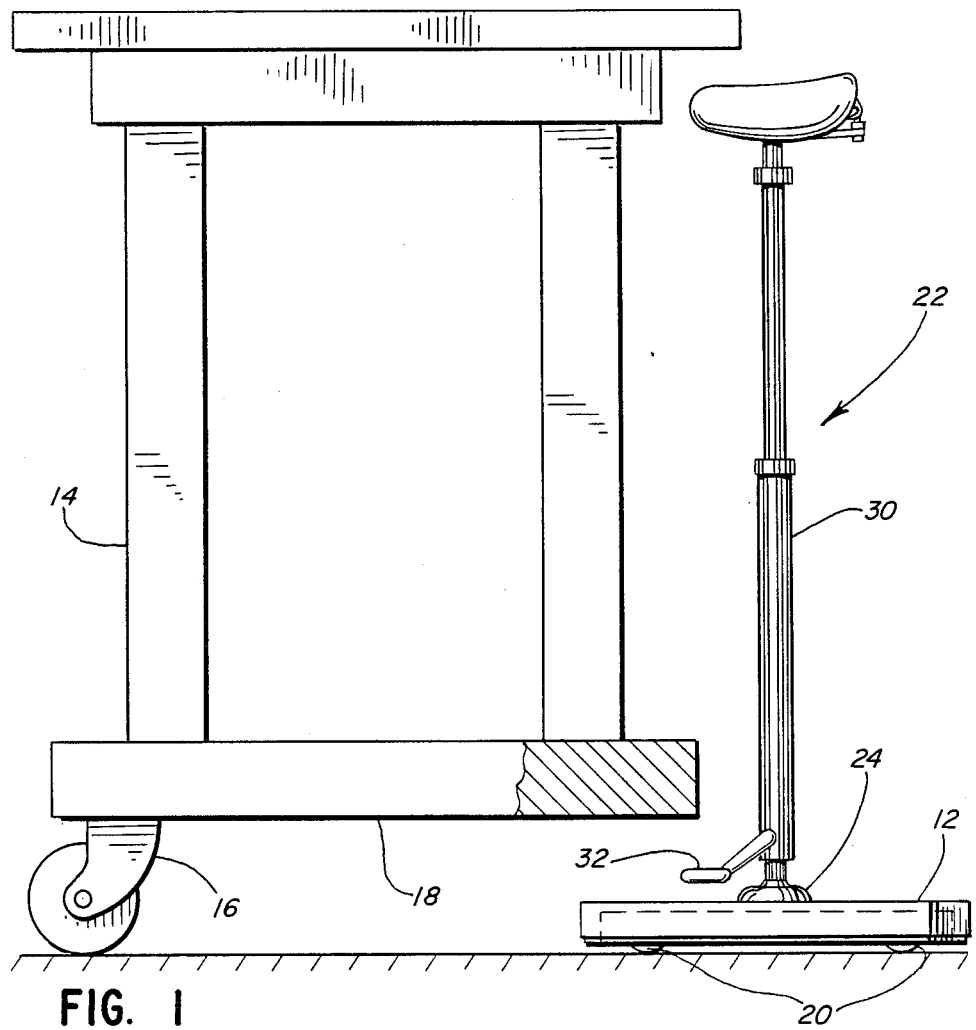
FIG. 1 is a side elevational view of the operating stool and an end view of an operating table.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the invention is to cover all modifications, equivalents, and alternatives falling within the spirit and scope of the invention as defined by the appended claims.

DESCRIPTION OF THE PREFERRED EMBODIMENTS

Turning now to the drawings and referring first to FIG. 1A, there is shown a side elevational view of the surgeon's operating stool 10. The stool 10 includes a base 12 which is preferably a generally flat, planar base having a minimum height so as to be received under an operating table 14. A standard operating table such as that illustrated at 14 includes a series of castor 16 arranged at the four corners of the operating table 14 so as to be movably positionable within the operating room. The base 18 of the operating table 14 sits directly on the castors 16 providing a space of approximately only 6 inches beneath the table 14. Therefore, in order for an operating stool such as that illustrated at 10 to be placed in close proximity to the operating table 14 the base 12 of the operating stool 10 should have a height less than the 6 inch opening provided at the base of the operating table. It should be appreciated that the base 12 is configured under the requirements of two competing design constraints. First, the base diameter should be as large as possible to add stability to the stool 10. Second, however, the base diameter should be as small as possible to allow the surgeon to more closely approach the operating table 14. Of course, the base 12 of the instant invention meets the rational behind both of the design constraints. A base 12 of relatively large diameter stabilizes the stool 10 to reduce the chance of undesirable tipping, yet by configuring the base to have a relatively low height, the base 12 passes under the operating table 14 for close positioning.

To accommodate further portability of the operating stool 10 a series of rollers 20 are provided beneath the lower surface of the base 12. The rollers 20 are of the multidirectional type allowing the operating stool 10 to be moved in any desired direction. The rollers 20 are, for example, of the same type and design as the castors 16 employed on standard operating tables 14. The rollers 20 are, of course, significantly reduced in size, but still provide 360° of rotation in a plane parallel to the base 12.

On the upper surface of the base 12 a support rod 22 extends generally perpendicularly upward from the base 12. The support rod 22 includes first and second end portions wherein the first end portion is connected to the approximate centroid of the base 12 by, for example, a standard pipe flange 24. The pipe flange 24 is in turn connected to the upper surface of the base 12 by a series of conventional bolts (not shown). The second end portion of the support rod 22 is connected to a standard bicycle seat 26.

To further add to the mobility of the surgeon, the bicycle seat 26 is connected to the supporting rod 22 through a standard rotary coupling 28. The rotary coupling 28 provides for rotation of the seat 26 in a plane generally parallel to the base 12. Likewise, the height of the seat 26 is infinitely adjustable to maximize the comfort and desired position of the operating surgeon. It should be noted that the height of the stool 10 is dissimilar to that of ordinary chairs where the thigh of a person sitting in a standard type chair is positioned approximately parallel to the floor. In an operating room environment it is more desirable for the surgeon to be positioned in a slightly crouched position, nearly standing. In fact, the seat 26 carries only a portion of the surgeon's weight. The remainder of the surgeon's weight is supported by his legs and feet positioned on the upper surface of the base 12. Typically during an operation, the surgeon assumes numerous and varied positions from fully seated on the operating stool 10, to fully standing on the base 12, and multiple positions therebetween.

Therefore, it is particularly desirable that the operating stool 10, while being easily positioned via the rollers 20, is stable and will not roll once positioned by the surgeon. To produce this desired effect the rollers 20 are configured to be generally collapsible within the base 12. When the surgeon positions himself on the stool 10, the wheels 20 retract into the base 12 preventing further movement until surgeon has dismounted the stool 10.

In order to accommodate a variety of desired height positions, the support rod 22 includes a hydraulic jack 30 with a pair of floor operated levers 32. Thus, the surgeon effects variations in height by pumping the foot pedal 32 to vary the hydraulic pressure and raise the seat 26.

Figure 2:
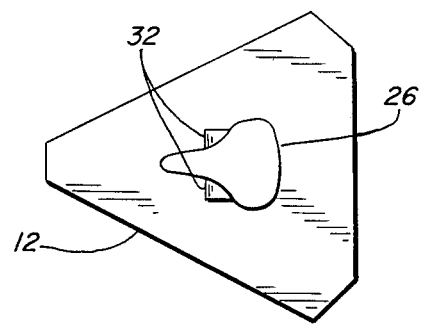
FIG. 2 is a top view of the operating stool.

Referring briefly to FIG. 2B, a top view of the stool 10 is illustrated. It can be seen that the base 12 is of a generally triangular configuration with the seat 26 substantially centrally located thereon.

Referring now to FIG. 5A, one embodiment of the collapsible roller mechanism is illustrated. The base 12 includes a first horizontal portion 34 which defines the upper surface of the base 12, and a vertical portion 36 extending about the periphery of the base 12. Additionally, the bottom edge of the vertical portion 36 includes a nonskid surface 38 adhered thereto. Accordingly, when the rollers 20 retract within the base 12 the nonskid surface 38 contacts the floor and prevents further movement of the operating stool 10. In the embodiment shown at FIG. 5A, the retractable mechanism includes a plate 40 movably mounted to the base 12 via a bolt 42 and spring 44. The bolt 42 threadably engages the horizontal portion 34 of the base 12 and passes through the plate 40. Thus, the bolt 42 acts as a guide pin to prevent rotation of the plate 40 relative to the base 12. However, the plate 40 is not vertically fixed relative to the bolt 42, but is free to slide up and down the bolt 42. Disposed about the bolt 42 between the plate 40 and horizontal portion of the base 12 is the coil spring 44. A pair of nuts 46 threadably engage the bolt 42 and are locked together to fix their position on the bolt 42. The plate 40 and spring 44 are thereby captured between the lower surface of the horizontal portion 34 and the pair of nuts 46. Therefore, the plate 40 is movable between two positions. A first position where the plate 40 engages the nuts 46 and a second position where the plate 40 is forced toward the lower surface of the horizontal portion 34 against the action of the coil spring 44.

A standard rotary castor 48 is bolted through the plate 40 near the edge of the plate 40 adjacent the vertical section 36 of the base 12. Accordingly, the plate 40 is normally biased to the first position where the roller 20 of the castor 48 engages the floor and the nonskid surface 38 does not. It should be appreciated that the bolt 42, spring 44, locked nuts 46, and castor 48 are repeated about the periphery of the plate 40 a plurality of times. Preferably, the triangular shape of the base 12 lends itself to three such arrangements positioned adjacent the three corners of the triangular base. The combined coefficient of the three springs 44 is selected, such that the weight of the operating stool 10 is insufficient to collapse the spring 44. Therefore, absent a person on the stool 10, the spring 44 supports the base 12 to prevent the nonskid surface 38 from engaging the floor and allows for positioning of the stool 10. Conversely, when a person takes a position on the stool 10, the combined weight of the person and the stool 10 overcomes the coefficient of the combined springs 44 and moves the plate 40 to the second position thereby engaging the antiskid surface 38 with the floor and preventing further movement. It should be appreciated that the upper surface of the base 12 provides area for receiving the feet of the person occupying the stool. Therefore, even when the person using the stool rises to a standing position, his weight remains on the stool 10 and the plate 40 remains in the second position. Thus, a surgeon using the stool 10 may safely assume any position on the stool 10 without fear of the stool 10 rolling unexpectedly.

Referring now to FIG. 6 An alternative embodiment of the collapsible mechanism is illustrated. Both embodiments of the collapsible mechanism includes similar parts and are therefore numbered identically where possible. In this embodiment the collapsible mechanism includes a hinge 50 having one of its leaves bolted to the lower surface of the horizontal portion 34. The other leaf of the hinge 50 is connected to a bracket 52. The bracket 52 has a generally L shape cross section with the vertical portion of the bracket being positioned at approximately a 45 degree angle with the horizontal portion of the bracket. The horizontal portion of the bracket 52 is connected to the castor 48. A stop 54 having an L shaped cross sectional configuration is bolted to the vertical portion 36 of the base 12. The stop 54 engages the lower surface of the 45 degree portion of the bracket 52 and prevents further movement toward the vertical portion 36 of the base 12. The bracket 52 is generally free to move in a direction generally toward the horizontal portion 34 of the base 12. A coil spring 56 is connected at it's first end portion to the stop 54 and at it's second end portion to the bracket 52. The spring 56, therefore, urges the bracket 52 in a direction toward the stop 54.

As in the first embodiment, the roller 20 is movable between first and second positions. The first position is where the roller 20 engages the floor and supports the base 12, such that the nonskid surface 38 does not engage the floor. The second position of the roller 20 is where both the roller 20 and the nonskid surface 38 engage the floor. The roller 20 is rotated slightly towards the horizontal portion 34 of the base 12, closing the hinge 50. The roller 20 is ordinarily located in the first position when no one is occupying the stool 10. The coefficient of the spring 56 is sufficient to support the weight of the stool 10 alone. However, in the presence of a person on the stool 10 the combined weight of the person and the stool 10 overcomes the spring 56, forcing the roller 20 to rotate toward the base 12. It should be appreciated that the collapsible mechanism illustrated in FIG. 2B is repeated about the periphery of the base 12. Preferably, the triangular shaped arrangement of the base 12 lends itself to the use of three such collapsible mechanisms at each corner of the triangle.

Turning now to FIG. 3 the support rod 22 and seat 26 are illustrated in greater detail. The seat 26 includes an outer covering 60 which is preferably formed of leather, vinyl, sheepskin, or the like. Within the outer covering 60 is a hard plastic shell 62 generally shaped in the bicycle seat configuration. Intermediate and upper surface of the hard shell 62 and the outer covering 60 is a collection of foam padding 64. The hard plastic shell 62 includes front and rear mounting points on a lower surface of the shell 62. The front mounting point 66 is connected through a suspension member 68 to the support rod 22. Similarly, the rear connection point is connected through a suspension member 70 to the support rod 22. In addition, the suspension member 70 is connected through a coil spring 72 to the rear connection point, thereby providing additional cushioning affect to the seat 26.

The support rod 22 includes a pipe 74 having a generally cylindrical configuration with a first end portion fitted into a clamping mechanism (not shown) and fastened thereto by means of friction and a nut and bolt arrangement 76. The second end portion of the pipe 74 is threaded on it's outer surface. The threaded portion of the pipe receives a ball bearing retainer 78. The pipe 74 and ball bearing retainer 78 slidably engage the rotary coupling 28. The rotary coupling 28 includes a housing 80 with a first bore 82 centered therein. A second bore 84 is coaxial with the first bore 82 and has a diameter slightly larger than the first bore diameter, forming a shoulder 86 about the junction of bores 84, 82. A plurality of ball bearings 88 are positioned within the housing 80 and are constrained against vertical movement by the shoulder 86 and ball bearing retainer 78. The bore 84 has a first end portion opening onto the upper surface of the rotary connection 28 and is threaded adjacent this first end portion. A retainer nut 90 is threaded into a bore 84 capturing the ball bearing retainer inside the housing 80 and thus preventing removal of the pipe 74. Accordingly, rotary movement of the seat 26 is carried by the ball bearings 88 on the shoulder 86. The rotary coupling 28 threadably engages an extension rod 92 of the hydraulic jack 30. Thus, it can be seen that movement of the extension rod 92 also results in vertical movement of the seat 26.

Vertical movement of the hydraulic jack 30 is controlled by the foot operated lever 32. Repeated pumping of the lever 32 results in an increased internal pressure in the hydraulic jack 30 forcing the extension rod 92 to move upward. Conversely, a foot operated lever 94 controls downward movement of the extension rod 92. Movement of the lever 94 downward vents the internal pressure of the hydraulic jack 30, thereby allowing the extension rod 92 to move downward into the hydraulic jack 30 and a corresponding movement of the seat 26 results.

The levers 32, 94 are mounted adjacent the base 12 allowing for easy foot operation. Accordingly, during the course of an operation, a surgeon readily adjusts the height of his seat 26 without compromising either his comfort or the sterile nature of the operating room. In particular, adjusting the height of the seat 26 does not require the surgeon to use his sterile hands.

Other aspects, objects, and advantages of this invention can be obtained from a study of the drawings, the disclosure, and the appended claims.

What is claimed is:

1. A surgeon's operating stool for supporting a user in both a standing and sitting position, comprising:
   a substantially planar base having upper and lower surfaces, said upper surface having a general configuration to receive the feet of a person using said stool in both a standing and sitting position and to allow a person to stand off the base with a portion of said base between the legs of the person and another portion behind the legs of the person, thereby permitting the person to stand with the stool generally maintained underneath the person, while providing a stable base which can be stood on and can stably support the stool in a sitting position of the person, said base further including a vertical portion extending around at least a part of a peripheral edge of said base with floor contact surface lowermost on said vertical portion;
   a support rod having first and second end portions, said first end portion being connected to the upper surface of said base and extending generally perpendicularly therefrom, said second end portion being connected to a seat; and a plurality of multidirectional rollers positioned below the lower surface of said base by moving means, said moving means for permitting said rollers and said base to be movable relative to one another between first and second preselected position in response to the presence of a person on said stool, said first position being with said wheels in contact with a support surface and said base being positioned a preselected distance above the support surface, said second position being with said wheels and said floor contact surface of said base in contact with the support surface, wherein said preselected distance is a maximum of six inches so that the base can fit beneath a low object and the stool can be positioned adjacent to the object.

2. A surgeon's operating stool, as set forth in claim 1, wherein said base is supported on said rollers by at least one spring.

3. A surgeon's operating stool, as set forth in claim 2, wherein said spring has a coefficient sufficient to support said base in said first preselected position.

4. A surgeon's operating stool, as set forth in claim 3, wherein said spring has a coefficient which is less than the coefficient required to support the base in said first position in response to the presence of a person on said stool.

5. A surgeon's operating stool, as set forth in claim 4, wherein said floor contact surface of said base includes a nonskid surface attached thereto and contacting the support surface in response to the base being in said second position.

6. A surgeon's operating stool, as set forth in claim 1, wherein said support rod includes a hydraulic jack having a lever adapted for varying the pressure in said jack, thereby adjusting the vertical height of said support rod.

7. A surgeon's operating stool, as set forth in claim 6, wherein said lever is positioned adjacent said base and adapted for operation by the foot of a person using said stool.

8. A surgeon's operating stool, as set forth in claim 1, wherein said seat is pivotally connected to said support rod to provide for rotation of said seat in a plane generally parallel to said base.

9. A surgeon's operating stool for supporting a user in both a standing and sitting position, comprising:

a substantially planar base having upper and lower surfaces, said upper surface being generally configured to receive the feet of a person using said stool in both a standing and sitting position and to allow a person to stand off the base with a portion of said base between the legs of the person and another portion behind the legs of the person, thereby permitting the person to stand with the stool generally maintained underneath the person, while providing a stable base which can be stood on and can stably support the stool in a sitting position of the person, said base further including a vertical position extending around at least a part of a peripheral edge of said base with a floor contact surface lowermost on said vertical portion;

a support rod having first and second end portions, said first end portion being connected to the upper surface of said base, said second end portion being connected to a seat; and a hydraulic jack disposed within said support rod intermediate said first and second end portions and having a housing connected to one of the first and second end portions and an extension rod connected to the other of said first and second end portions, said hydraulic jack having a lever adapted for varying the pressure in said jack, thereby adjusting the vertical height of said support rod.

10. A surgeon's operating stool, as set forth in claim 9, wherein said lever is positioned adjacent said base and adapted for operation by the foot of a person using said stool.

11. A surgeon's operating stool, as set forth in claim 9, including a plurality of multidirectional rollers positioned below the lower surface of said base by moving means, said moving means for permitting said rollers and said base to be movable relative to one another between first and second preselected positions in response to the presence of a person on said stool, said first position being with said wheels in contact with a support surface and said base being positioned preselected distanced above said support surface, said second position being with said wheels and the lower surface of said base in contact with the support surface, wherein said preselected distance is a maximum of six inches so that the base can fit beneath a low object and the stool can be positioned adjacent to the object.

12. A surgeon's operating stool, as set forth in claim 11, wherein said base is supported on said rollers by at least one spring.

13. A surgeon's operating stool, as set forth in claim 12, wherein said spring has a coefficient sufficient to support said base and said first preselected position.

14. A surgeon's operating stool, as set forth in claim 13, wherein said spring has a coefficient which is less than the coefficient required to support the base in said first position in response to the presence of a person on said stool.

15. A surgeon's operating stool, as set forth in claim 14, wherein the lower surface of said base includes a nonskid surface attached thereto and contacting the support surface in response to the base being in said second position.

16. A surgeon's operating stool, as set forth in claim 9, wherein said seat is pivotally connected to said support rod to provide for rotation of said seat in a plane generally parallel to said base.

17. A surgeon's operating stool for supporting a user in both a standing and sitting position, comprising:

a substantially planar base having upper and lower surfaces, said upper surface being generally configured to receive the feet of a person using said stool in both a standing and sitting position and to allow a person to stand off the base with a portion of said base between the legs of the person and another portion behind the legs of the person, thereby permitting the person to stand with the stool generally maintained underneath the person, while providing a stable base which can be stood on and can stably support the stool in a sitting position of the person, said base further including a vertical portion extending around at least a part of a peripheral edge of said base with a floor contact surface lowermost on said vertical portion;

a support rod having first and second end portions, said first end portion being connected to the upper surface of said base, said second end portion being connected to a seat;

a plurality of multidirectional rollers positioned below the lower surface of said base by moving means, said moving means for permitting said rollers and said base to be movable relative to one another between first and second preselected positions in response to the presence of a person on said stool, said first position being with said wheels in contact with a support surface and said base being positioned a preselected positions in response to the presence of a person on said stool, said first position being with said wheels in contact with a support surface and said base being positioned a preselected distance above said support surface, said second position being with said wheels and the lower surface of said base in contact with the support surface, wherein said preselected distance is a maximum of six inches so that the base can fit beneath a low object and the stool can be positioned adjacent to the object; and a hydraulic jack dispersed within said support rod intermediate said first and second end portions and having a housing connected to one of the first and second end portions and an extension rod connected to the other of said first and second end portions, said hydraulic jack having a lever adapted for varying the pressure in said jack, thereby adjusting the vertical height of said support rod.

18. A surgeon's operating stool, as set forth in claim 1, wherein said moving means comprises a generally horizontal plate onto which said plurality of multidirectional rollers are secured, a plurality of guide bolts fixed to said base that extend through holes in said plate to fix said plate in only a single axial direction of said guide bolts, and springs means acting between said base and said plate to bias said base and said plate apart.

19. A surgeon's operating stool, as set forth in claim 1, wherein said moving means comprises a hinge means for each one of said multidirectional rollers, each said hinge means including a leaf attached to said base and a second leaf attached to a roller, a step means fixed to said vertical portion of said base adjacent each hinge means for stopping a downward pivotal motion of said second leaf, and a bias means to urge said second leaf toward said stop means.

20. A surgeon's operating stool as set forth in claim 11, wherein said base is substantially triangular in configuration to include a front wall, a rear wall of greater length than said front wall and sidewalls angling between said front and rear walls, said support rod being connected to said upper surface at a point substantially centrally thereof, said lever for said hydraulic jack extending outwardly from said support rod toward said front wall in closely spaced relationship to the upper surface of said base.

* * * * *